United States Patent [19]

Farley

[11] Patent Number: 5,730,773
[45] Date of Patent: *Mar. 24, 1998

[54] CHEMICAL DISPENSING DEVICE AND METHOD

[76] Inventor: James J. Farley, Wassex House Apt. 412, 505 E. Lancaster Ave., St. David, Pa. 19087

[*] Notice: The term of this patent shall not extend beyond the expiration date of Pat. No. 5,620,499.

[21] Appl. No.: 753,676

[22] Filed: Dec. 27, 1996

Related U.S. Application Data

[63] Continuation of Ser. No. 373,890, Jan. 17, 1995, Pat. No. 5,620,499.
[51] Int. Cl.⁶ ............................................ C05G 5/00
[52] U.S. Cl. .................. 71/64.11; 71/64.13; 71/900; 47/48.5; 424/409; 424/484; 424/485; 504/116
[58] Field of Search ............. 71/11, 64.11, 64.13, 71/900; 47/48.5, 62, 64; 424/409, 484, 485; 504/116

[56] References Cited

U.S. PATENT DOCUMENTS 5,620,499 4/1997 Farley .................... 71/64.11

Primary Examiner—Ferris Lander
Attorney, Agent, or Firm—LaMorte & Associates

[57] ABSTRACT

The present invention is a device and method for selectively dispensing at least one target compound into a selected environment. A target compound is dissolved within an elastomer compound in a concentration that supersaturates the elastomer compound. The elastomer compound is then shaped into a selected form that is conducive to placement within the selected environment. The target compound within the elastomer compound begins to bloom to the surface of the elastomer compound where it is exposed to the surrounding environment. The bloom of the target compound into the surrounding environment continues until the concentration of the target compound within the elastomer compound reaches its saturation point. As such, the duration of the bloom of the target compound from the elastomer compound can be regulated by the concentration of the target compound within the elastomer compound, the volume of the elastomer compound and the surface area of the elastomer compound.

4 Claims, 2 Drawing Sheets

1

CHEMICAL DISPENSING DEVICE AND METHOD

RELATED APPLICATIONS

This application is a continuation of U.S. patent application Ser. No. 08/373,890, filed Jan. 17, 1995, entitled CHEMICAL DISPENSING DEVICE AND METHOD now U.S. Pat. No. 5,620,499, Apr. 15, 1997.

BACKGROUND OF THE INVENTION

1. Field of the Invention

The present invention relates to an elastomer compound used to slowly dispense a fertilizer compound or other desired substance into a targeted environment over a period of time. More particularly, the present invention relates to such elastomer compounds where the desired substance is dissolved within the elastomer compound, at a supersaturated concentration, causing the desired substance to slowly bloom to the surface of the elastomer compound and be dispensed into the surrounding environment.

2. Description of the Prior Art

Bloom is a term of art in elastomers that refers to the migration of a liquid or solid material from the composition of the elastomer to the surface of the elastomer. Bloom is caused when a dissolved ingredient is added to the elastomer compound recipe in a concentration that is in excess of its solubility. In such a situation, if the conditions for crystallization of the supersaturated ingredient are more favorable in the presence of air than within the body of the elastomer, then the supersaturated ingredient will separate out of the elastomer compound and crystallize at the surface of the polymer as it contacts the surrounding air. The change in the saturation concentration gradient created by the surface crystallization causes the supersaturated ingredient to migrate from within the elastomer compound toward the exterior surfaces of the elastomer compound. The bloom of the supersaturated ingredient will continue over time until the concentration of the blooming ingredient within the elastomer compound falls to a concentration corresponding to the saturation point of the elastomer compound. Bloom ceases when the concentration of the migrating substance in the elastomer compound becomes equal to its solubility at a given temperature.

The slow dispensing of a chemical compound, over a prolonged period of time, is a useful process in many industries. One of the most obvious of these industries is that of agriculture. Dispensing fertilizers and/or pesticides on plants is often an expensive and labor intensive operation. Additionally, conventional applications of fertilizer and pesticides must be repeated because the potency of such compounds is often time sensitive. Furthermore, environmental factors such as rain may wash such compounds away from the plants before they have had an opportunity to perform their intended function. Additionally, too much fertilizer or pesticide may have an adverse effect on plants by causing fertilizer burn or adding unacceptable levels of poisons to the fruit born by such plants.

In an attempt to reduce the time and labor involved with dispensing fertilizer and pesticides to plants, the prior art has seen the development of slow dispensing devices, whereby upon one application, small amounts of fertilizer or pesticides are made available to plants over an extended period of time. In the prior art, such slow dispensing devices typically include a biodegradable material impregnated with a fertilizer or pesticide product. As the biodegradable material decomposes, the fertilizer and/or pesticide is released into the surrounding soil. Such prior art devices are exemplified by U.S. Pat. No. 3,320,695 to Moore, Jr., entitled DEGRADABLE POLYOLEFIN MULCHING FILM, U.S. Pat. No. 1,554,865 to Magoon, entitled DEVICE FOR TREATING SOIL and U.S. Pat. No. 4,063,919 to Grano, Jr., entitled FERTILIZER RODS.

The problems associated with such biodegradable fertilizer dispensing devices is that they are time consuming and labor intensive to install around plants. Furthermore, the amount of fertilizer or pesticide released by such devices is dependent entirely upon the environment in which they contact. For instance, if such devices were positioned in rich soil that had a high moisture content and a high bacterial presence, the prior art devices would decompose very rapidly and the fertilizer or pesticide released would not last throughout the entire growing season. Adversely, if such devices were positioned on dry soil with a very low moisture content and bacterial presence, the prior art devices may not adequately decompose and therefore may not properly dispense the fertilizer or pesticide.

In other prior art products, the osmotic effect of water passing through a fertilizer or pesticide containing medium is used to dispense the fertilizer or pesticide around desired plants. One such prior art device is taught by U.S. Pat. No. 4,224,048 to Pendergast, entitled OSMOTIC FERTILIZER PRODUCT AND FERTILIZATION METHOD. In the Pendergast patent, a fertilizer is shown impregnated within a water swellable polymer. The polymer absorbs water administered to the plant, dilutes fertilizer into the water and passes the water/fertilizer solution on to the plant with a controlled capillary action. The disadvantage of this design is that the water swellable polymer must be buried under the soil near each plant. For this reason, the application of the water swellable polymer is highly labor intensive. Additionally, with the use of a water swellable polymer, the dispensing of fertilizer is directly proportional to the moisture content of the soil. If the moisture content is high, osmosis occurs and large amounts of fertilizer are released. Adversely, if the soil has a very low moisture content, almost no fertilizer is released to the plant.

In U.S. Pat. No. 5,105,577 to Hedges, entitled ARTIFICIAL MULCH CHIPS, a thermoplastic material is shown with a textured surface. The thermoplastic material is then coated with an active ingredient, such as an insecticide, and is thrown upon the soil in the region of a garden. Once in the garden, the effects of wind and water cause diffusion of the active ingredient into the surrounding environment. No mechanism is provided to control the rate of diffusion of the active ingredient over time.

In U.S. Pat. No. 4,166,340 to Pluenneke, entitled POT LINING METHOD WITH RECLAIMED TIRE FIBERS, a polymer is used to enhance the quality of soil without the addition of a fertilizer compound. In the Pluenneke patent, shreds of an automotive tire are used in the bottom of a potted plant. The tire pieces provide good drainage characteristics and provide micronutrients of sulphur, iron, zinc and manganese to the plant. The tire pieces must be buried proximate the roots of a plant, as such the process is highly time consuming and labor intensive.

Although the prior art does show the use of various elastomer products in the controlled dispensing of fertilizers and pesticides, the prior art fails to show fertilizers or pesticides dissolved within the elastomer such that the added fertilizer or pesticide supersaturates the elastomer compound and blooms to the exterior of the elastomer over a known period of time. Such a migration of fertilizer or pesticide to the exterior of the elastomer compound is not dependent upon available moisture in the soil or the bacterial content of the soil. Consequently, fertilizer or pesticide can be slowly and consistently dispensed over a period of time regardless of the environment surrounding the plant.

It is a further object of the present invention to produce a product that can be administered around plants above the soil, thereby reducing the labor involved in supplying fertilizers to plants.

SUMMARY OF THE INVENTION

The present invention is a device and method for selectively dispensing at least one target compound into a selected environment. A target compound is dissolved within an elastomer compound in a concentration that supersaturates the elastomer compound. The elastomer compound is then shaped into a form that is conducive to placement within the selected environment. The target compound within the elastomer compound begins to bloom to the exterior surfaces of the elastomer compound where it is exposed to the surrounding environment. The bloom of the target compound into the surrounding environment continues until the concentration of the target compound within the elastomer compound reaches its saturation point. As such, the duration of the blooming of the target compound from the elastomer compound can be regulated by the concentration of the target compound within the elastomer compound, the volume of the elastomer compound and the surface area of the elastomer compound.

In one preferred embodiment, the present invention device and method can be used to dispense fertilizer to plants. In such an application, various fertilizer compounds can be dissolved within an elastomer compound. The elastomer compound can then be extruded, molded or otherwise shaped into strips which can be placed on the ground near plants. The fertilizer compounds will bloom from the strips and will pass into the soil where they are absorbed by the roots of the plants. The strips can be manufactured so that the bloom of the fertilizer compounds from the strips will last throughout the growing season of the plants, thereby slowly dispensing fertilizer to the plants regardless of soil conditions.

BRIEF DESCRIPTION OF THE DRAWINGS

The invention will be more fully understood by referring to the following detailed specification, the above background and the claims set forth herein, when taken in conjunction with the drawings appended hereto, wherein;

DETAILED DESCRIPTION OF THE DRAWINGS

Figure 1:
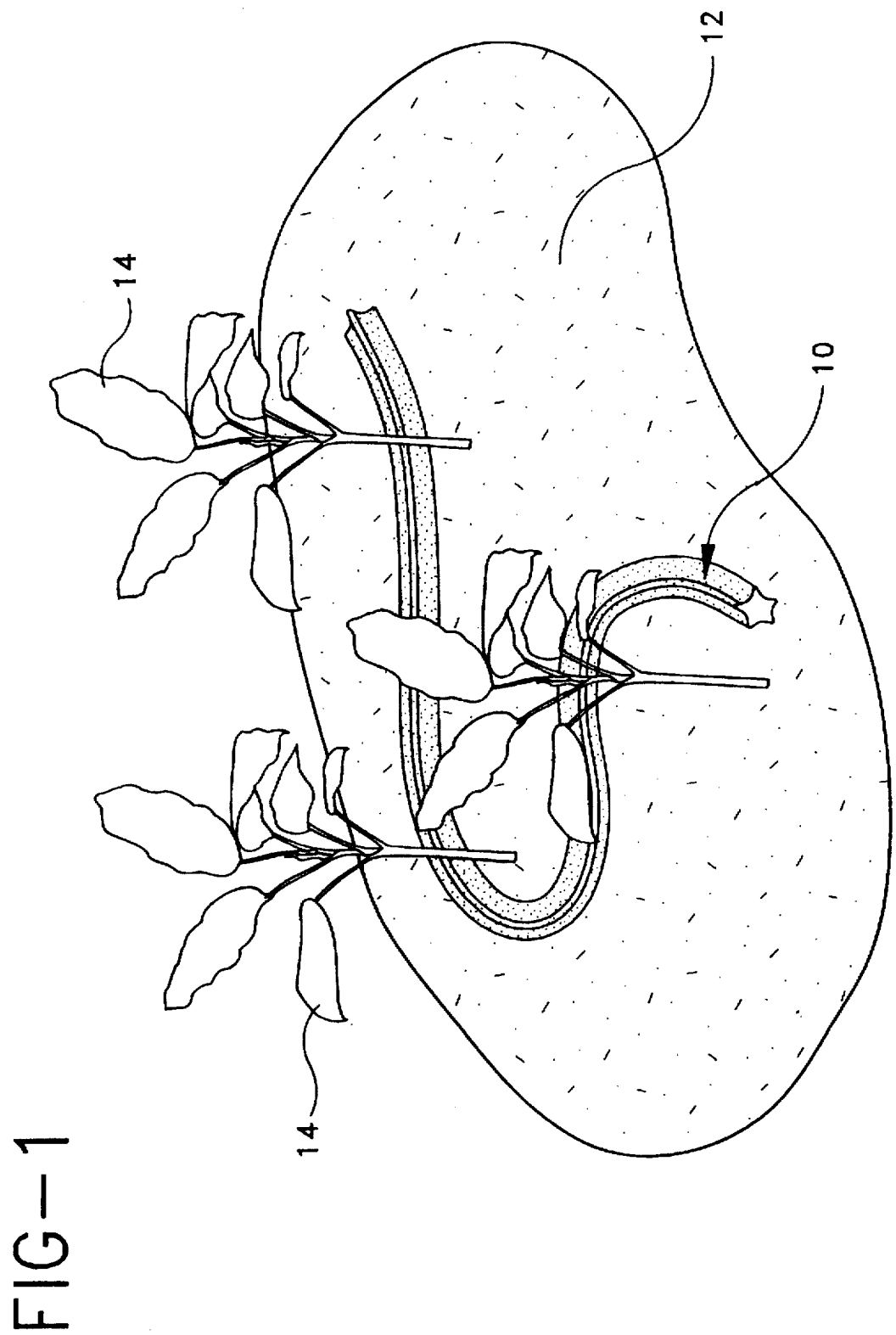
FIG. 1 shows a perspective view of one preferred embodiment of the present invention, shown in conjunction with plants to facilitate discussion and consideration.

Although the present invention can be used in many different applications where it is desired to dispense a chemical compound in a controlled manner over an extended period of time, it is especially suitable for use in dispensing fertilizers in agriculture. Accordingly, the present invention will be described in connection with the controlled application of fertilizers in an agricultural environment.

The phenomenon of bloom can be produced in a variety of natural and synthetic elastomers. To create bloom within an elastomer, a chemical or chemical compound that is soluble within the base elastomer must be added to the elastomer compound in a concentration that supersaturates the elastomer compound. Additionally, in order for bloom to occur, the added chemical or chemical compound must have the characteristic of precipitating out of solution more energetically in the presence of air than within the body of the elastomer compound. If both criteria are present, the chemical or chemical compound dissolved in the elastomer formulation will slowly separate from solution at the surface of the elastomer compound. The resulting change in the concentration gradient of the dissolved chemical, causes the dissolved chemical or chemical compound to actively migrate toward the exterior surfaces of the elastomer. The amount of material that eventually migrates to the surfaces of the elastomer compound is controlled by the amount of oversaturation, the volume of the elastomer compound and the surface area of the elastomer compound. As such, the bloom of a dissolved chemical or chemical compound from the elastomer will continue until the concentration of the blooming material within the elastomer compound falls to its saturation point. The process of bloom is not instantaneous. Rather, depending upon such variables as the type of elastomer, surface area, volume and degree of supersaturation, bloom may occur within a period of time from hours to years before an equilibrium within the elastomer compound is finally achieved.

The phenomenon of bloom can be created in many types of natural and synthetic elastomers. Such elastomers include, but are not limited to, natural rubber (NR), isoprene rubber (IR), butadiene rubber (BR), chloroprene rubber (CR), isobutylene-isoprene rubber (IIR), nitrile-butadiene rubber (NBR), butadiene-acrylonitrile rubber, styrene-butadiene rubber (SBR), ethylene-propylene copolymer (EPR), ethylene-propylene-diene terpolymer (EPDM) and silicone rubbers. Although any of these elastomers may be used in forming the present invention, the present invention is preferably formed utilizing natural rubber. Natural rubber is a preferred embodiment because it is readily shaped, has a high susceptibility to bloom and is soluble with many different types of commercially available fertilizers. Referring to Table 1 below, a preferred embodiment for the present invention rubber compound recipe is shown.

TABLE 1

| INGREDIENT | PERCENTAGE BY WEIGHT |
|---|---|
| Natural Rubber | 35.0–65.0 |
| Clay | 20.0–45.0 |
| Processing Oil | 0.0–05.0 |
| Colorant | 0.0–05.0 |
| Fertilizer | 3.0–06.0 |
| Sulfur | 0.05–1.0 |
| Zinc dimethyl dithiocarbamate | 1.5–03.0 |
| 2-mercaptobenzothiazole | 1.0–03.0 |
| Antioxidant | 0.0–01.0 |
| Paraffin | 0.0–04.0 |

The fertilizer of Table 1 can be any commercially available fertilizer chemical or chemical compound. The selection of the fertilizer is dependent upon the solubility of that fertilizer in the remainder of the rubber compound recipe. As such, it will be understood that different fertilizers may be used as the rubber compound recipe is varied, because different fertilizers are more highly soluble in different recipes. Many commercially available fertilizer compounds are soluble in natural rubber compounds. Such fertilizer compounds include primary nutrients such as nitrogen, phosphorus and potassium, secondary nutrients such as calcium and magnesium and micronutrients such as iron, manganese, copper, zinc, boron and molybdenum. Common fertilizer compounds such as ammonium nitrate and monoammonium phosphate have been found to be soluble in varying degrees in the natural rubber compound recipe of Table 1. As such, the amount of fertilizer added to the rubber compound recipe depends upon the fertilizer chosen.

As has been previously described, in order to facilitate the phenomenon of bloom, the compound that is blooming has to be added to the rubber formulation in a concentration that supersaturates the formulation. In the present invention, it is desired to have the fertilizer to bloom out of the rubber formulation. As such, the fertilizer must be added to the rubber compound recipe in a concentration that supersaturates the rubber formulation. As will be recognized by a person skilled in the art, the solubility of one compound into another is typically temperature dependent. As such, the amount of fertilizer added to the rubber compound recipe will depend upon the temperature of the formulation during mixing. Since it is desirable to supersaturate the rubber compound recipe with the added fertilizer, it is desirable to mix the fertilizer into the rubber compound recipe at a relatively high processing temperature, thereby increasing the degree of supersaturation available in the final compound.

However, the processing temperature during mixing should not be high enough to cause any curing of the formulation.

The clay of Table 1 can be any clay additive conventionally added to natural rubber compounds. Such clays are well known in the art and are added to natural rubber compounds to increase abrasion resistance, increase tensile strength and increase stiffness. Other well known materials, such as fine particle zinc oxides, calcium carbonates, calcium silicates, amorphous hydrated silicon dioxide, pure silicon dioxides and fine-particle magnesium carbonate, barium sulfate or carbon black can also be used in combination with, or in place of, the preferred clay additive.

The processing oil of Table 1 is also a well known additive to natural rubber compounds. Processing oils of many different types are conventionally used in rubber compound recipes to decrease viscosity of the compound, aid in the dispersion of fillers, reduce calendar shrinkage and/or provide lubrication to aid in extrusion or molding of the compound.

The sulfur of Table 1 is used as the vulcanizing agent in curing the rubber compound. The use of sulfur as a vulcanizing agent is extremely well known and practiced in the art of natural rubber compounds. As the vulcanizing agent, the sulfur cross links the various polymer chains within the natural rubber creating the elastomer. Many natural rubber compounds require a variety of operations that produce and require heat, such as mixing, extruding, calendaring, molding and the like. As such, it is desirable not to have an appreciable amount of polymer cross-linking to be established before these operations are performed. To prevent the added sulfur of Table 1 from causing premature polymer cross-linking, a delayed action accelerator is added to the present invention natural rubber compound.

In the rubber compound recipe of Table 1, the accelerator used is zinc dimethyl dithiocarbamate in combination with 2-mercaptobenzothiazole (MBT). It should be understood that either accelerator can be used by itself. Similarly, any other well known accelerator conventionally used in curing natural rubber, such as bis (2,2-benzothiazolyl) disulfide (MBTS), benzothiazolesulfenamides, 2-(4-morpholinylthio) benzothiazole and the like can also be used.

It should be understood that if a chosen fertilizer compound does not rapidly dissolve within the rubber compound recipe of Table 1, a retarding agent, sometimes called a prevulcanization inhibitor, may be added to the rubber compound recipe to slow the vulcanization reaction. Such retardants can prevent vulcanization of the rubber compound mixing, calendaring and other processing steps, thereby providing the added fertilizer with additional time to dissolve within the rubber compound. The retardants used can be any conventional retardant used in natural rubber compounds such as N-(cyclohexylthio)phtalimide (CTP), sulfonamide derivatives, salicylic acid or the like.

In accordance with Table 1, an antioxidant is added to the natural rubber compound. When natural rubber is harvested, it contains natural antioxidants, proteins and complex phenols that protect the rubber from deterioration over time. These natural protectants are destroyed during vulcanization. As such, synthetic protectants are added to the rubber compound recipe to ensure an adequate service life in the cured rubber. There are many antioxidants conventionally used in association with natural rubber. Any such known antioxidant may be used in the present invention rubber compound recipe.

A colorant may be added to the rubber compound recipe in accordance with the listing in Table 1. The colorant added controls the color of the final rubber product. For example, black colorants can be used if it is desirable to have a black rubber product. Many black colorants are known and have been widely used in the automotive tire industry. A common colorant is carbon black, however any other known colorant, for any color, may also be used.

Paraffin may be added to the rubber compound recipe of Table 1 as a precipitating agent. Paraffin dissolves in natural rubber and readily blooms from the rubber if added to the rubber in a supersaturated concentration. The bloom of the paraffin from the rubber compound promotes the bloom of the fertilizer from the rubber compound. Furthermore, the migration of paraffin to the surface of the rubber compound during bloom, helps in the migration of the added fertilizer to the surface of the rubber compound. The addition of paraffin within the rubber compound also reduces the saturation point of the rubber compound. As such, a supersaturation of fertilizer can be more readily achieved.

It will be understood that the rubber compound recipe set forth in Table 1 is merely exemplary and other recipes and/or other concentrations can be used provided the added fertilizer supersaturates the resulting rubber compound. Additionally, other ingredients such as stabilizers, softeners, extenders, stiffeners, bonding agents and the like may also be added to the rubber compound recipe in order to produce a final rubber compound with desired physical characteristics.

The rubber compound made from the recipe set forth in Table 1 can be molded, extruded or otherwise worked into any size or shape. Referring to FIG. 1, it can be seen that in one preferred embodiment, the rubber compound can be extruded into long strips 10 which can be placed on the surface of the soil 12 proximate the stems of targeted plants 14. Since the rubber compound strips 10 can be made of a natural rubber compound, the strips 10 can be made to be highly flexible. As such, the rubber compound strips 10 can be placed upon the soil 12 in any desired orientation including a path that would serpentine between targeted plants 14 as shown. It will be understood that the present invention rubber compound need not be molded into long strips 10, as shown, but may be molded into any desired shape or form. For instance, the present invention rubber compound can be molded into ornamental designs that can be placed in a garden. Alternatively, the rubber compound can be molded into artificial mulch chips which can be placed throughout a garden or around plants as part of landscaping. In an alternative embodiment, the rubber compound can be molded into large flat sheets that can be placed throughout a garden to help deter the growth of weeds.

Figure 2:
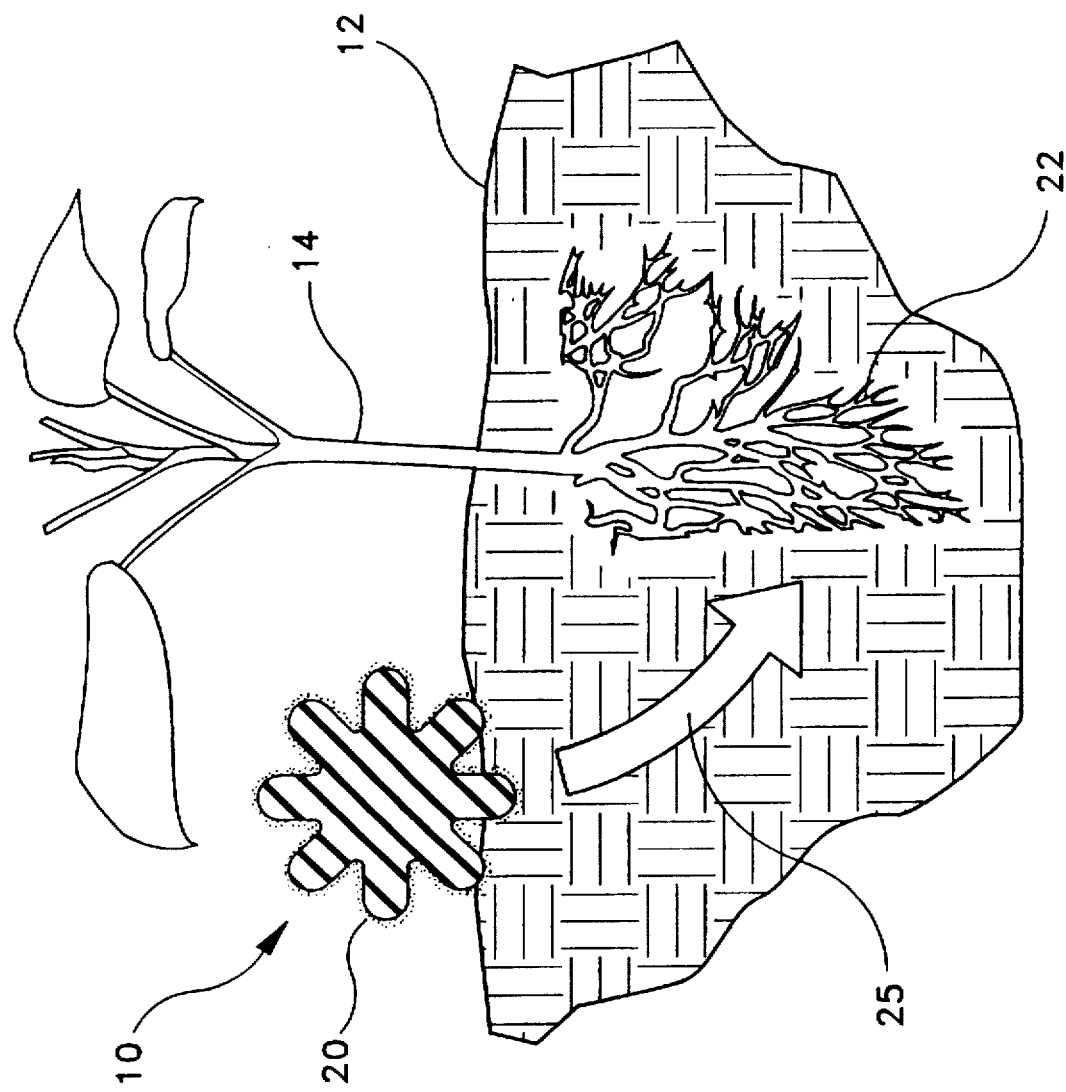
FIG. 2 shows a cross-sectional view of one preferred embodiment of the present invention shown in conjunction with a plant to help illustrate operation.

Referring to FIG. 2, it can be seen that in the preferred embodiment, the rubber compound strips 10 are molded to have a star-shaped cross-sectional profile. Such a configuration is readily made using a star-shaped extrusion die. By configuring the rubber compound strips 10 with a star-shaped profile, the surface area of the rubber compound strips 10 that is exposed to the surrounding air can be increased.

As has been previously described, bloom will occur when a supersaturated additive to an elastomer compound precipitates out of solution with the elastomer compound more readily in the presence of air than within the body of the elastomer. As such, it should be understood that the phenomenon of bloom can be largely reduced or delayed by keeping the supersaturated elastomer in an air free enclosure. Upon the extrusion of the rubber compound strips 10, the strips 10 can be shrink wrapped in cellophane or the like. Consequently, bloom can be substantially delayed until the rubber compound strips 10 are purchased by a consumer and the cellophane coating is removed, thereby exposing the surfaces of the strips 10 to air.

In FIG. 2 it can be seen that the fertilizer contained in the original rubber compound recipe of Table 1, blooms to the surface of the rubber compound strips 10. As the fertilizer blooms, it precipitates out of solution and crystallizes on the surface of the rubber compound strips 10 so as to form a pellicle layer 20. Rain, irrigation water, wind and the like then cause the crystallized fertilizer contained within the pellicle layer 20 to flow onto the soil 12. Once the fertilizer is dispensed onto the soil 12, the roots 22 of the targeted plants 14 can absorb the fertilizer in the conventional manner as depicted by arrow 25.

The bloom of fertilizer will continue within the rubber compound strips 10 until the concentration of fertilizer within the rubber compound strips 10 reaches the saturation point and the rubber compound ceases to be supersaturated with the added fertilizer. As has been previously mentioned, rubber compounds can be formed so that bloom occurs from a period of time from hours to years. In the preferred embodiment, the concentration of fertilizer within the rubber compound is calculated so that bloom will continue for a few months (i.e. the growing cycle of the target plants 14). Consequently, small amounts of fertilizer will be dispensed to the targeted plants 14 throughout the entire growing season of the plants 14. As the growing season of the targeted plants 14 ends, and the fertilizer reaches an equilibrium point within the rubber compound, bloom ceases and the rubber compound strips 10 can be removed and discarded.

For plants that require fertilizer year round, rubber compound strips 10 can be manufactured that last for a desired period (i.e. six months, one year, etc.). As such, the rubber compound strips 10 can be replaced on an annual or semi-annual basis. Additionally, different fertilizers can be added to the rubber compound strips 10 for different seasons, thereby allowing different fertilizers to be dispensed by periodically changing the strips 10. The bloom of fertilizer from the present invention rubber compound lasts as long as the fertilizer does not reach a saturation equilibrium within the rubber compound. As such, bloom continues depending upon the volume of rubber compound, concentration of fertilizer and exposure of the rubber compound to air. Despite the long period of bloom, the rate of bloom is not constant, but is rather exponential, being more rapid at first and slowing over time. This complements agricultural plants very well, where more fertilizer is needed during the initial growing phase of the plants than is required during the later, maturing periods of the plants. As such, the present invention strips 10 are best dispensed during the growing phase of plants so that fertilizer can be provided throughout the life of the plant in the needed proportions.

In the shown embodiment of FIG. 2, the star-shaped profile of the rubber compound strips 10 increases the surface area of the strips 10. As such, more of the rubber compound material is exposed to the surrounding air, thereby increasing the rate of bloom and the volume of fertilizer dispensed over time. It will therefore be understood that by changing the shape of rubber compound strips 10, the rate of bloom can also be controlled. As such, different shaped strips may be manufactured for different types of plants, whereby the type of fertilizer, the concentration of fertilizer, the volume of the rubber compound and the shape of the extruded strips can be made to match the specific fertilizer needs of differing plants.

Although the above described embodiment of the present invention rubber compound is believed to represent the best mode of the present invention, it will be understood that many described chemical components of the rubber compound recipe have known functional equivalents. Additionally, proportions used within the described recipe may be changed and undescribed chemical compounds may be added to the rubber compound by a person skilled in the art. All such modifications and additions are intended to be covered by the scope of this invention as set forth in the appended claims.

What is claimed is:

1. A device for dispensing at least one target compound into a surrounding environment over a period of time, wherein said at least one target compound is selected from a group consisting of fertilizers, pesticides and herbicides, said device comprising:

a substantially water insoluble elastomer compound, said elastomer compound having said at least one target compound completely dissolved therein in a concentration in excess of the solubility of said at least one target compound at ambient temperature and pressure, whereby said at least one target compound precipitates out of solution at a predetermined rate for said period of time and is dispensed into the said surrounding environment in a controlled manner.

2. The device according to claim 1, wherein a secondary compound is included within said elastomer compound in a concentration in excess of the solubility of said secondary compound at ambient temperature and pressure, wherein said secondary compound readily precipitates out of solution and promotes the bloom of said at least one target compound into said surrounding environment.

3. The device according to claim 1, wherein said elastomer compound includes a rubber polymer selected from a group consisting of natural rubber, isoprene rubber, butadiene rubber, chloroprene rubber, isobutylene-isoprene rubber, nitrile-butadiene rubber, styrene-butadiene rubber, ethylene-propylene copolymer, ethylene-propylene-diene terpolymer and silicone rubber.

4. The device according to claim 1, wherein said elastomer compound includes natural rubber and said secondary compound includes paraffin.

* * * * *